United States Patent
Yong

(10) Patent No.: US 8,491,855 B2
(45) Date of Patent: Jul. 23, 2013

(54) SAFETY, BIODEGRADABLE BIOLOGICAL SAMPLE COLLECTION SYSTEM

(76) Inventor: Peter A. K. Yong, Torrance, CA (US)

(*) Notice: Subject to any disclaimer, the term of this patent is extended or adjusted under 35 U.S.C. 154(b) by 89 days.

(21) Appl. No.: 12/947,780

(22) Filed: Nov. 16, 2010

(65) Prior Publication Data

US 2011/0097250 A1    Apr. 28, 2011

Related U.S. Application Data

(63) Continuation-in-part of application No. 11/505,770, filed on Aug. 16, 2006, now abandoned, which is a continuation-in-part of application No. 11/191,300, filed on Jul. 28, 2005.

(60) Provisional application No. 61/261,512, filed on Nov. 16, 2009.

(51) Int. Cl.
 *B01L 3/00* (2006.01)

(52) U.S. Cl.
 USPC ........................................................ 422/547

(58) Field of Classification Search
 USPC ................................................ 422/102, 547
 See application file for complete search history.

(56) References Cited

U.S. PATENT DOCUMENTS

| | | | |
|---|---|---|---|
| 57,256 A | 8/1866 | Meglone | |
| D28,532 S | 5/1898 | Wagner | |
| D34,474 S | 5/1901 | Greiner | |
| 1,494,367 A | 5/1924 | Morgan | |
| 1,534,939 A | 4/1925 | Fuge | |
| 1,597,513 A | 8/1926 | Dever | |
| 1,668,315 A * | 5/1928 | Hein | 604/241 |
| 2,628,054 A | 2/1953 | Fazakerley | |
| 3,850,203 A | 11/1974 | Shobert | |
| 4,024,857 A | 5/1977 | Blecher et al. | |
| 4,109,530 A | 8/1978 | Kim | |
| 4,134,573 A | 1/1979 | Messinger | |
| 4,276,889 A | 7/1981 | Kuntz et al. | |
| 4,347,749 A | 9/1982 | Heintze | |
| 4,494,581 A | 1/1985 | Gordon | |
| 4,557,274 A * | 12/1985 | Cawood | 600/573 |
| 4,569,090 A | 2/1986 | Muller | |
| 4,709,399 A | 11/1987 | Sanders | |
| 4,769,215 A | 9/1988 | Ehrenkranz | |
| D304,795 S | 11/1989 | Klopp | |

(Continued)

FOREIGN PATENT DOCUMENTS

| | | |
|---|---|---|
| DE | 3325736 A1 | 1/1995 |
| JP | 55-96436 | 7/1980 |
| WO | WO 2005/094685 A1 | 10/2005 |

OTHER PUBLICATIONS

WO 2011/060452, Jan. 3, 2011 ISR.

(Continued)

*Primary Examiner* — Bobby Ramdhanie

(57) ABSTRACT

Collection containers for urine and other liquid samples are described. The collection containers include a handle attachment which allows a handle to be attached. Use of the handle reduces the likelihood that patients will soil their hands while providing urine and other samples into the collection container. In addition, the handle attachment allows a portion of the sample to be transferred through it and into a handle that also acts as a test container. The collection containers are also biodegradable and reduce the amount of waste generated.

18 Claims, 10 Drawing Sheets

U.S. PATENT DOCUMENTS

| | | | |
|---|---|---|---|
| D306,648 S | 3/1990 | Jones et al. |
| 5,028,988 A | 7/1991 | Porter et al. |
| D320,331 S | 10/1991 | Paone |
| 5,058,787 A | 10/1991 | Chou |
| 5,060,411 A | 10/1991 | Uhlman |
| 5,147,342 A | 9/1992 | Kane et al. |
| 5,165,639 A | 11/1992 | Knuppe |
| 5,171,146 A | 12/1992 | Guerci |
| 5,171,300 A | 12/1992 | Blake, III et al. |
| 5,174,965 A | 12/1992 | Jones et al. |
| D334,804 S | 4/1993 | Jones et al. |
| D335,179 S | 4/1993 | Jones et al. |
| D335,180 S | 4/1993 | Jones et al. |
| 5,202,094 A | 4/1993 | Jones et al. |
| D335,346 S | 5/1993 | Jones et al. |
| D335,708 S | 5/1993 | Jones et al. |
| 5,215,533 A | 6/1993 | Robb |
| 5,219,083 A * | 6/1993 | Liebert et al. ............ 215/247 |
| 5,267,791 A | 12/1993 | Christian et al. |
| 5,328,484 A | 7/1994 | Somers et al. |
| 5,342,328 A | 8/1994 | Grossman et al. |
| 5,422,076 A | 6/1995 | Jones |
| 5,429,803 A | 7/1995 | Guirguis |
| D364,458 S | 11/1995 | Jones et al. |
| 5,471,994 A | 12/1995 | Guirguis |
| 5,535,785 A | 7/1996 | Werge et al. |
| 5,558,840 A | 9/1996 | Jones et al. |
| D376,297 S | 12/1996 | Jacobson |
| 5,766,136 A * | 6/1998 | Cawood ............ 600/573 |
| 5,775,546 A | 7/1998 | Buehler |
| 5,839,946 A | 11/1998 | Hertz |
| 5,849,505 A | 12/1998 | Guirguis |
| 5,915,384 A | 6/1999 | Grossman et al. |
| 6,013,230 A | 1/2000 | Kuchar |
| 6,171,261 B1 | 1/2001 | Niermann et al. |
| 6,171,287 B1 | 1/2001 | Lynn et al. |
| 6,210,909 B1 | 4/2001 | Guirguis |
| 6,235,010 B1 | 5/2001 | Wilkinson et al. |
| 6,277,646 B1 | 8/2001 | Guirguis et al. |
| 6,281,008 B1 | 8/2001 | Komai et al. |
| 6,350,254 B1 | 2/2002 | Wilkinson et al. |
| 6,409,528 B1 | 6/2002 | Bodnar |
| 6,409,704 B1 | 6/2002 | Tsai |
| 6,447,730 B1 | 9/2002 | Kuchar |
| 6,485,691 B1 | 11/2002 | Jones |
| 6,508,987 B1 | 1/2003 | Wilkinson et al. |
| 6,509,164 B1 | 1/2003 | Guirguis |
| 6,572,827 B2 | 6/2003 | Wilkinson et al. |
| 6,616,893 B1 | 9/2003 | Pham |
| 6,651,987 B1 | 11/2003 | Hosaka |
| 6,799,694 B1 | 10/2004 | Scott |
| 2002/0132369 A1 | 9/2002 | Wilkinson et al. |
| 2004/0085215 A1 | 5/2004 | Moberg et al. |
| 2005/0132821 A1 | 6/2005 | Furey et al. |
| 2007/0025886 A1 | 2/2007 | Yong |
| 2007/0217959 A1 | 9/2007 | Balestracci et al. |
| 2008/0240986 A1 | 10/2008 | Chang |

OTHER PUBLICATIONS

International Search Report for WO 2006/020421, dated Sep. 19, 2006.
PCT/US2005/026847, Oct. 23, 2006 ISR/WO.
EP 05784101.7, Sep. 24, 2010 search report and opinion.
PCT/US2010/056906, Jan. 12, 2011 ISR/WO.
PCT/US2010/056904, Mar. 10, 2011 ISR/WO.
U.S. Appl. No. 12/947,786, filed Oct. 14, 2011 non-final.
European search report for 05784101.7, dated Sep. 17, 2010.
International Search Report for WO 2011/060451, dated Feb. 28, 2011.

* cited by examiner

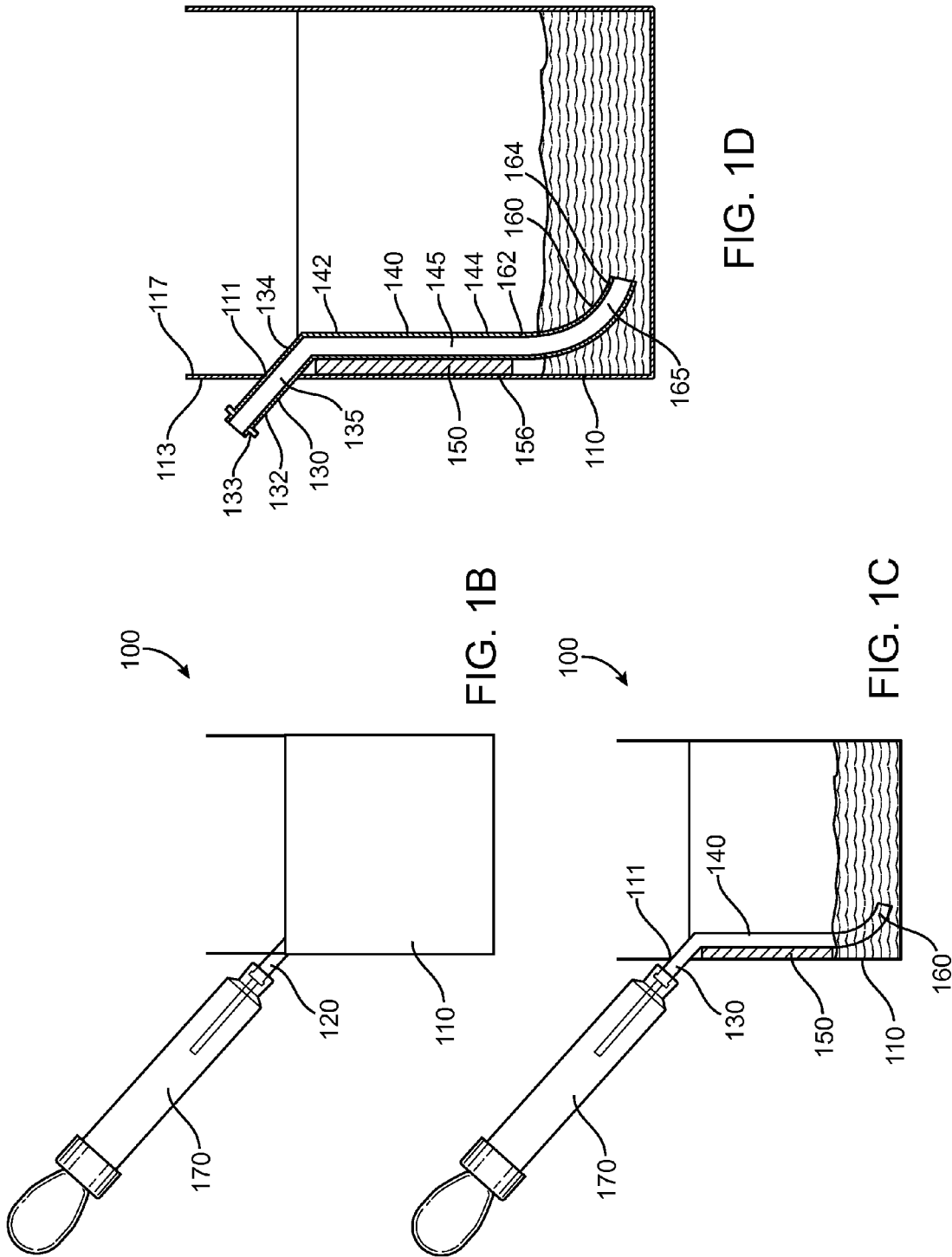

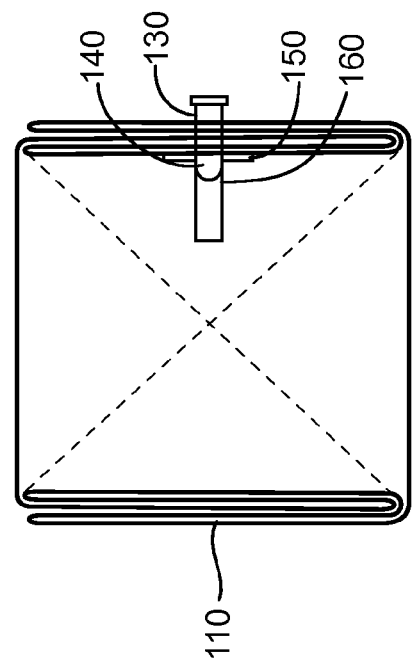
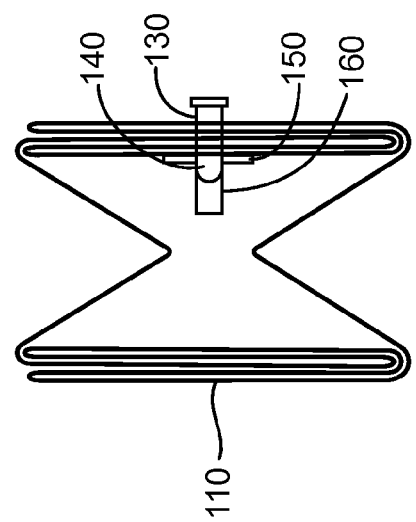
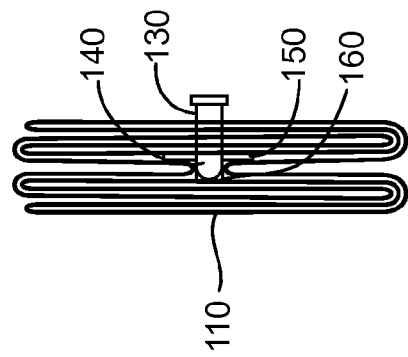

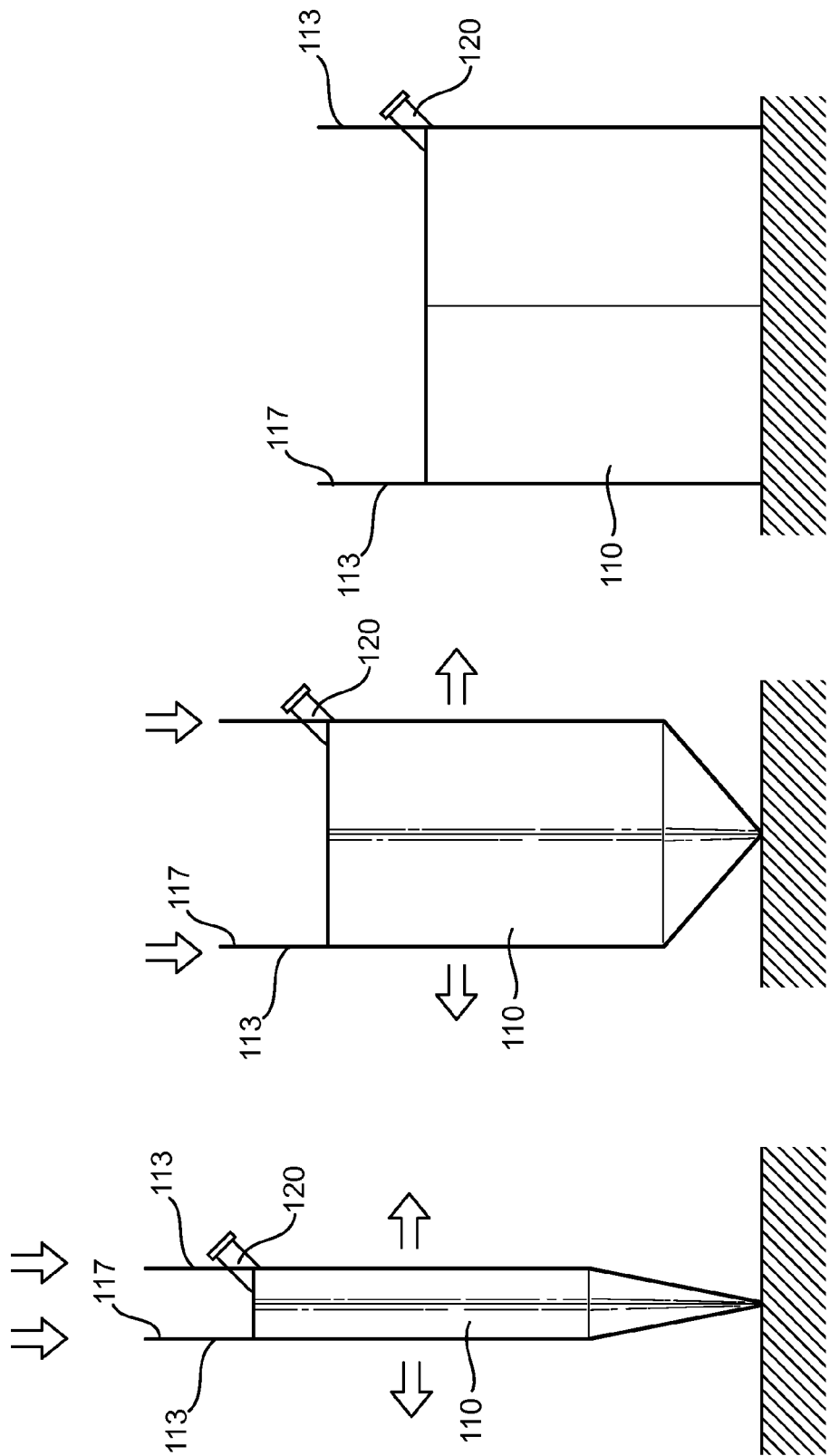

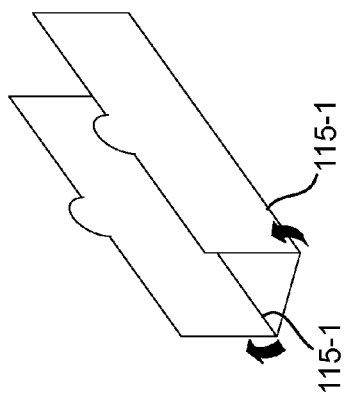
FIG. 5C
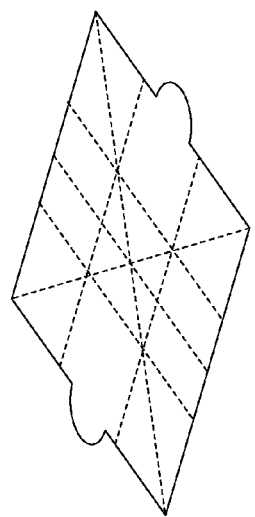
FIG. 5B
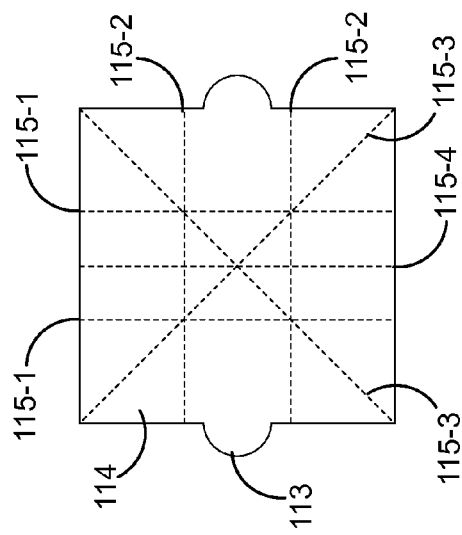
FIG. 5A
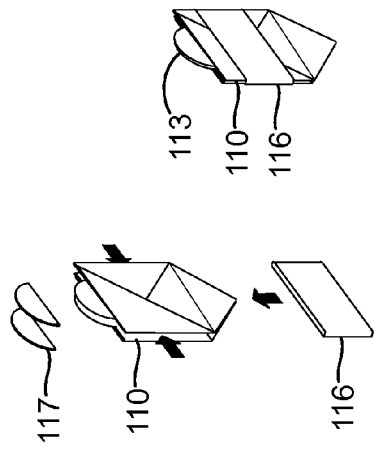
FIG. 5H
FIG. 5G
FIG. 5F
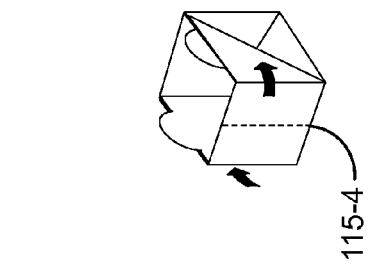
FIG. 5E
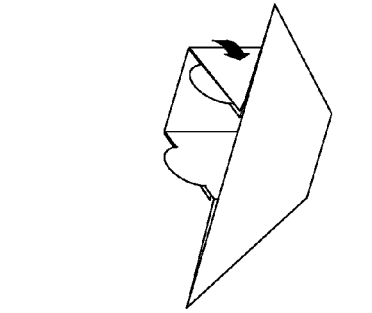
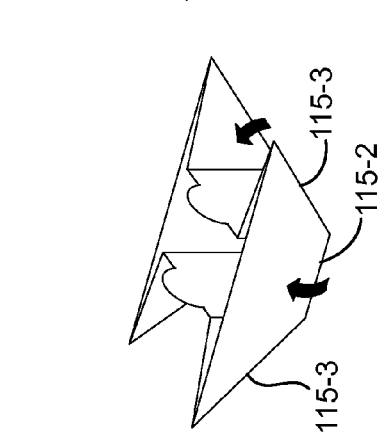
FIG. 5D

SAFETY, BIODEGRADABLE BIOLOGICAL SAMPLE COLLECTION SYSTEM

CROSS-REFERENCE TO RELATED APPLICATIONS

This application claims the benefit of U.S. provisional application Ser. No. 61/261,512, filed Nov. 16, 2009. This application is also a continuation-in-part of U.S. patent application Ser. No. 11/505,770, filed Aug. 16, 2006, now abondoned, which is a continuation-in-part of U.S. patent application Ser. No. 11/191,300, filed Jul. 28, 2005.

BACKGROUND

The collection of urine and other samples for testing is typically performed by giving a patient a plastic cup in which to urinate or provide a sample. However, patients often inadvertently soil their hands when attempting to urinate or provide a sample into a cup. Female patients can find it especially challenging to maneuver a cup into position and keep it in place in a dignified fashion to provide a urine sample without soiling their hands.

After the patient has provided a urine or other sample, a portion of the sample is typically transferred into other containers such as a test tube for laboratory work. This can be a very tedious process with large numbers of samples for analysis in the lab. This presents the opportunity for the sample to spill or splash, or otherwise create exposure to a potentially hazardous sample.

The plastic cups typically used for urine collection are single-use and not biodegradable. This generates a substantial amount of waste. They also cannot be stacked inside one another because this would contaminate the interiors of the cups. Consequently, the plastic cups take up substantial space for storage and transport.

What is needed is a collection cup which will make urine collection a more dignified procedure, by facilitating urinating or providing a sample into the cup. What is also needed is a collection cup which will reduce the likelihood that a patient will soil their hands while urinating or providing a sample into the cup.

What is needed is a collection cup which will facilitate transferring the sample into other containers for laboratory work. What is also needed is a collection cup which will reduce the chances for the sample to spill or splash while transferring the sample to other containers.

What is needed is a collection cup which will reduce the amount of waste generated and reduce the costs of disposal. What is also needed is a collection cup which takes up less space for storage and transport.

SUMMARY

A collection container comprises a receptacle for collecting a liquid sample. The receptacle includes an open top. The collection container also comprises a handle extension including a proximal end and a distal end. The handle extension includes a first lumen. The collection container also comprises a fitting coupled to the proximal end of the handle extension. The fitting is capable of being coupled to a mating device. The collection container also comprises a middle section having a proximal end and a distal end. The proximal end of the middle section is coupled to the distal end of the handle extension. The middle section includes a second lumen in fluid communication with the first lumen. The collection container also comprises an attachment plate coupled to middle section and to the receptacle. The collection container also comprises an aspiration tube having a proximal end and a distal end. The proximal end of the aspiration tube is coupled to the distal end of the middle section. The aspiration tube has a third lumen in fluid communication with the second lumen and with an interior of the receptacle. The distal end of the aspiration tube reaches at least near a bottom of the receptacle.

BRIEF DESCRIPTION OF THE DRAWINGS

FIGS. 1A-1D show one embodiment of a collection container 100.

FIGS. 2A-2C, 3A-3C, and 4A-4C show one embodiment of receptacle 110.

FIGS. 5A-5H show one embodiment of a method for making receptacle 110.

DETAILED DESCRIPTION

Figure 1A:
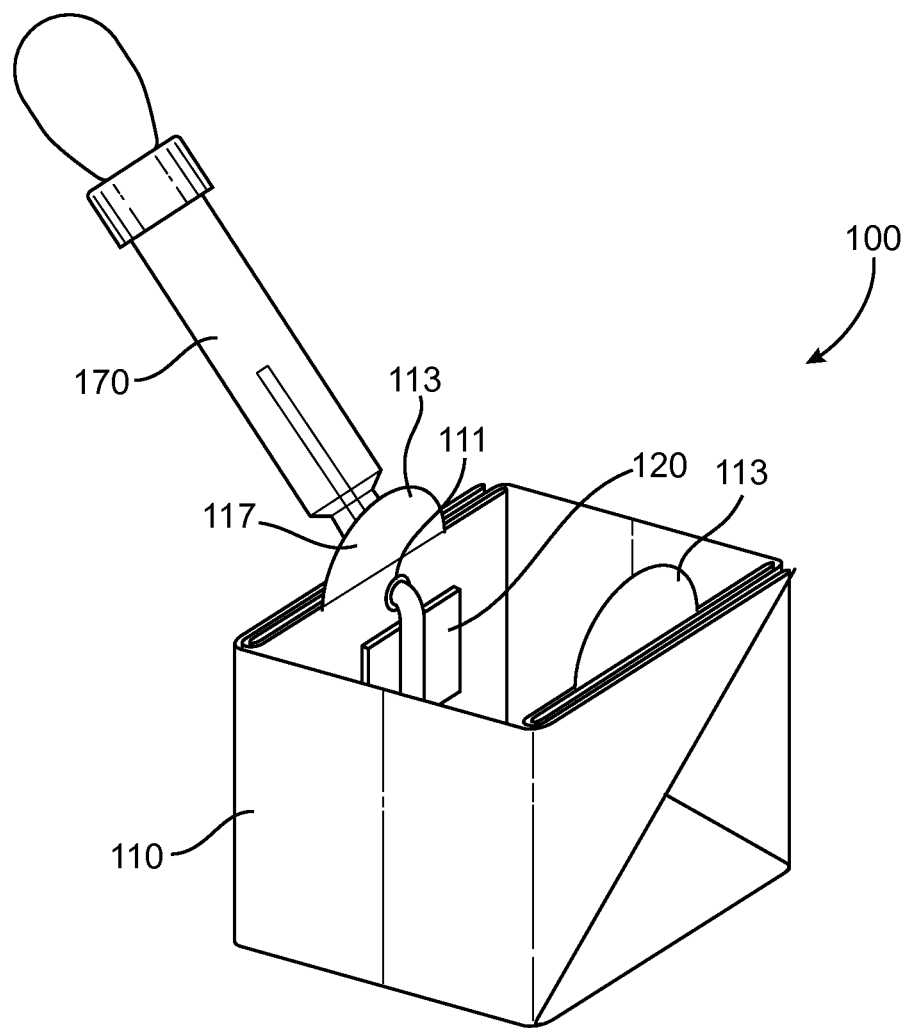

FIGS. 1A-1D show one embodiment of a collection container 100. FIG. 1A shows a perspective view of collection container 100. FIG. 1B shows a side view of collection container 100. FIG. 1C shows a cutaway view of collection container 100. FIG. 1D shows a magnified view of handle attachment 120.

Collection container 100 includes a receptacle 110, a handle attachment 120, and a handle 170.

Receptacle 110 is used for collecting urine, blood, saliva, or other liquid samples. Receptacle 110 has an open top, and may be square in shape. Alternatively, receptacle 110 may be cylindrical, rectangular, or any other suitable shape. Receptacle 110 may be made of a recyclable or biodegradable material such as paper. Receptacle 110 may be collapsible for storage and transport. Receptacle 110 may include a port 111. Port 111 may be formed in a side of receptacle 110. Alternatively, port 111 may be formed in a bottom or any other suitable location of receptacle 110.

Handle attachment 120 includes a handle extension 130, a middle section 140, an attachment plate 150, and an aspiration tube 160.

Handle extension 130 includes a proximal end 132 and a distal end 134. Handle extension 130 includes a lumen 135. Handle extension 130 may be made of a substantially rigid material such as plastic or other suitable material. A fitting 133 is coupled to proximal end 132 of handle extension 130. Fitting 133 may be a luer-lock connector or any other suitable connector. Fitting 133 is capable of being coupled to a mating fitting on a mating device such as handle 170. Fitting 133 may be a female luer connector which is capable of being coupled to a male luer connector on a mating device. Handle extension 130 and handle 170 may extend from receptacle 110 at an upward or ergonomic angle, which improves accessibility and allows the patient to maneuver and position receptacle 110, and maintain receptacle 110 in a substantially horizontal position during the collection of liquid samples.

Middle section 140 includes a proximal end 142 and a distal end 144. Proximal end 142 of middle section 140 is coupled to distal end 134 of handle extension 130. Middle section 140 includes a lumen 145 in fluid communication with lumen 135 of handle extension 130. Middle section 140 may be made of a substantially rigid material such as plastic or other suitable material.

Middle section 140 includes an attachment plate 150 which allows middle section 140 to be coupled to receptacle 110. Attachment plate 150 may be coupled to receptacle 110 with a double-sided tape 156. Alternatively, attachment plate 150 may be coupled to receptacle 110 with an adhesive, tape, staple, rivet, or any other suitable method or device which will not contaminate or react with a liquid sample in receptacle 110. Attachment plate 150 may be flat, curved, or otherwise configured to substantially follow the contour or shape of receptacle 110.

Aspiration tube 160 includes a proximal end 162 and a distal end 164. Proximal end 162 of aspiration tube 160 is coupled to distal end 144 of middle section 140. Aspiration tube 160 includes a lumen 165 in fluid communication with lumen 145 of middle section 140. Aspiration tube 160 may be made of a flexible material such as plastic or other suitable material. Aspiration tube 160 may be of sufficient length to reach the bottom or near the bottom of receptacle 110. Aspiration tube 160 may thus be able to reach most or all of a liquid sample in receptacle 110, even when the sample volume is very low.

Attachment plate 150 may be coupled to a side of receptacle 110. Alternatively, attachment plate 150 may be coupled to a bottom or any other suitable location of receptacle 110. Attachment plate 150 may be coupled to an inside of receptacle 110, and handle extension 130 may pass through port 111. Alternatively, attachment plate 150 may be coupled to an outside of receptacle 110, and aspiration tube 160 may pass through port 111.

Handle 170 may serve as a transporting and dispensing device, such as the handles described in U.S. patent application Ser. No. 2006/0039833, which is incorporated by reference. A portion of a liquid sample in receptacle 110 may be transferred to handle 170 by creating a vacuum within handle 170 and drawing the liquid sample through lumens 165, 145, and 135 and into handle 170. After a portion of the liquid sample has been transferred, handle 170 may be uncoupled from handle extension 130. Alternatively, handle 170 may be an elongate member made of a recyclable and/or biodegradable material such as cardboard or paper.

Figure 2C:
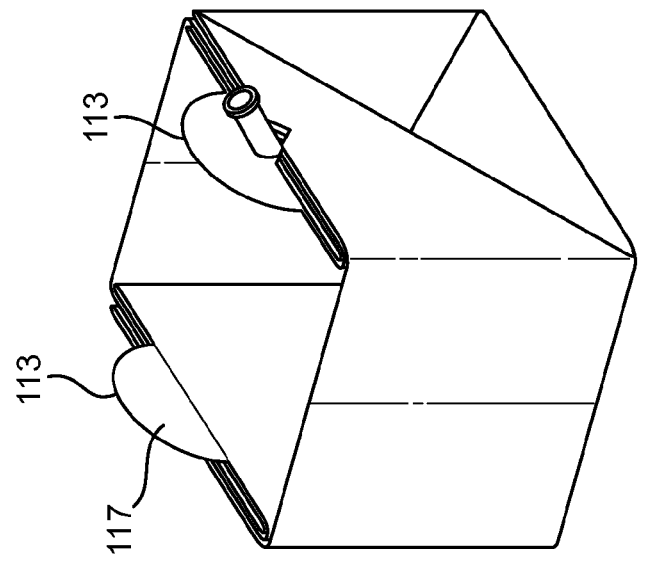
Figure 2B:
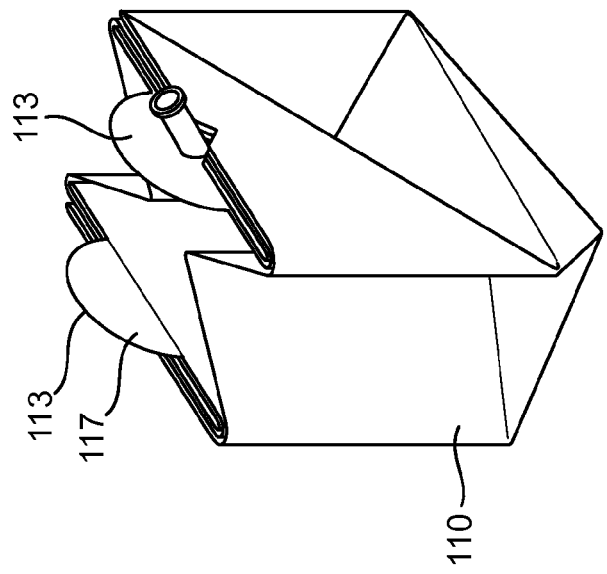
Figure 2A:
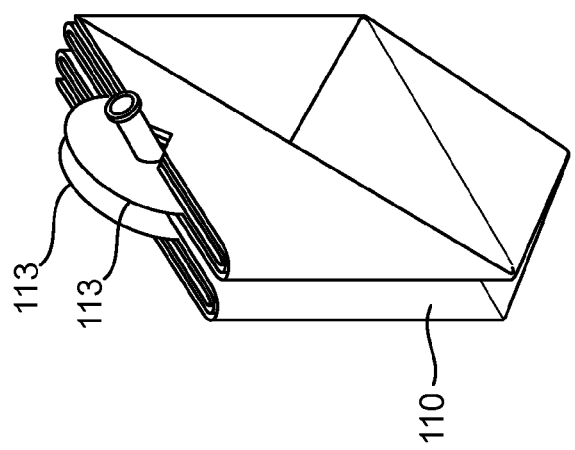

FIGS. 2A-2C, 3A-3C, and 4A-4C show one embodiment of receptacle 110. FIGS. 2A-2C show perspective views of receptacle 110 in a collapsed, intermediate and expanded configurations. FIGS. 3A-3C show top views of receptacle 110 in a collapsed, intermediate, and expanded configurations. FIGS. 4A-4C show side views of receptacle 110 in a collapsed, intermediate, and expanded configurations.

Receptacle 110 has a collapsed configuration and an expanded configuration. In the collapsed configuration, receptacle 110 may be stored, packaged, and/or transported. The collapsed configuration also helps to keep the inside of receptacle 110 clean or sterile until ready for use. In the expanded configuration, receptacle 110 may receive a liquid sample. Receptacle 110 may include tabs 113. Tabs 113 facilitate the expansion of receptacle 110 from the collapsed configuration to the expanded configuration. Tabs 113 may be formed as part of receptacle 110. Alternatively, tabs 113 may be formed separately and coupled to receptacle 110. Tab covers 117 may cover the inside of tabs 113 to help keep the inside of receptacle 110 clean. Tab covers 117 may be peel-off sheets that stick on the inside of tabs 113 or sleeves that fit over tabs 113. Tab covers 117 may be removed after use.

To expand receptacle 110 from the collapsed configuration to the expanded configuration, tabs 113 may be grasped and the pointed bottom of receptacle 110 brought into contact with a substantially flat surface such as a table, sink, leg, or other suitable surface. Next, tabs 113 may be used to push the bottom of receptacle 110 against the substantially flat surface, which forces the walls of receptacle 110 outwards into the expanded configuration. A uniform, progressive force may be used to "flip" the walls of receptacle 110 outwards.

Receptacle 110 may be made of a single sheet of paper, cardboard, or other disposable and/or biodegradable material. Receptacle 110 may be coated or treated so that is resistant or impervious to liquid samples. For example, receptacle 110 may be coated with a wax or bonded to a plastic layer.

FIGS. 5A-5H show one embodiment of a method for making receptacle 110.

FIGS. 5A-5B show a single sheet 114 of sufficiently thick paper or cardboard. A square sheet 114 may be used, with protruding tabs 113. Alternatively, a rectangular, circular, irregular, or any other suitable shape may be used. Sheet 114 includes a bottom, two pairs of opposing walls, and four corners. Sheet 114 may have folds 115 as indicated by the dotted lines. Alternatively, sheet 114 may be scored as indicated by the dotted lines. A first pair of folds 115-1 divides sheet 114 into thirds along its vertical axis. A second pair of folds 115-2 divides the sheet 114 into thirds along its horizontal axis. A third pair of folds 115-3 divides sheet 114 into halves along both diagonal axes. A fourth fold 115-4 divides sheet 114 into halves along its vertical axis. Folds 115 may be positioned to create receptacle 110 with taller sides, a wider bottom, or other desired dimensions. Tabs 113 may be located along the edge of sheet 114.

FIG. 5C shows the left and right thirds of sheet 114 folded up along the first pair of folds 115-1 to create the first pair of opposing walls.

FIG. 5D shows the top and bottom thirds of the square piece folded up along the second pair of folds 115-2 to create the second pair of opposing walls. Also, the four corners of sheet 114 are folded along the third pair of folds 115-3 into triangular shapes.

FIG. 5E shows the first two corners folded in and affixed to the walls. FIG. 5F shows the second two corners folded in and affixed to first two corners and/or the walls. The corners may be affixed with an adhesive, tape, staples, rivets, or any other suitable method or device.

FIG. 5G shows two opposing corners and the bottom being folded along the fourth fold 115-4 to collapse receptacle 110.

FIG. 5H shows a sleeve 116 placed around receptacle 110 to maintain receptacle 110 in the collapsed configuration. Tab covers 117 may also be attached to tabs 113.

Figure 6A:
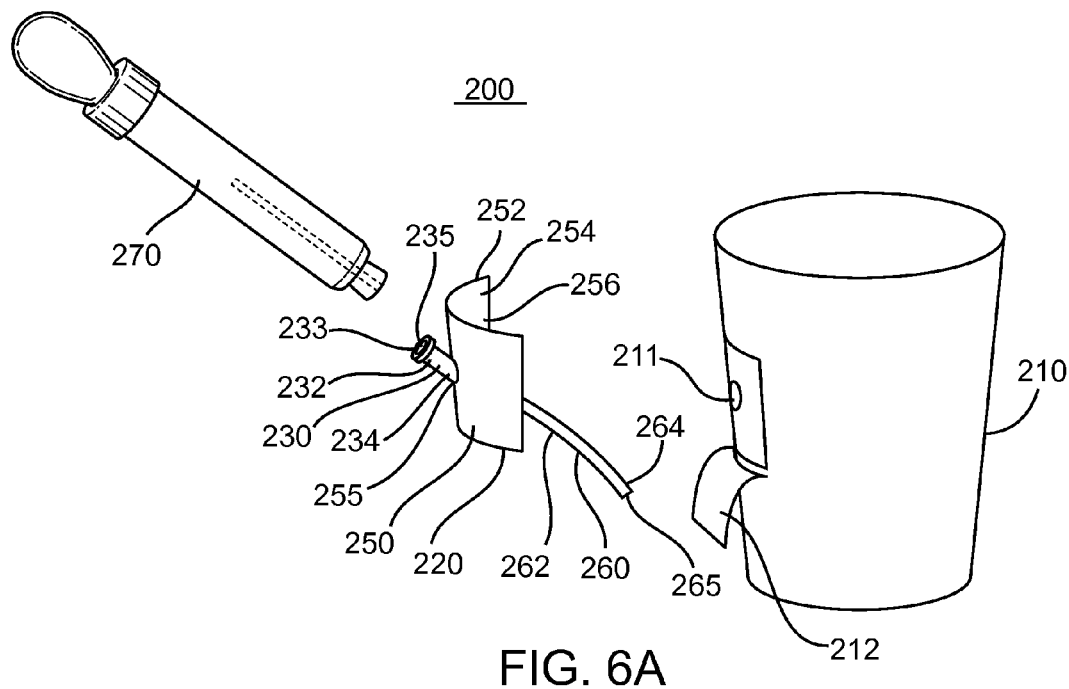
FIGS. 6A-6B show another embodiment of a collection container 200.
Figure 6B:
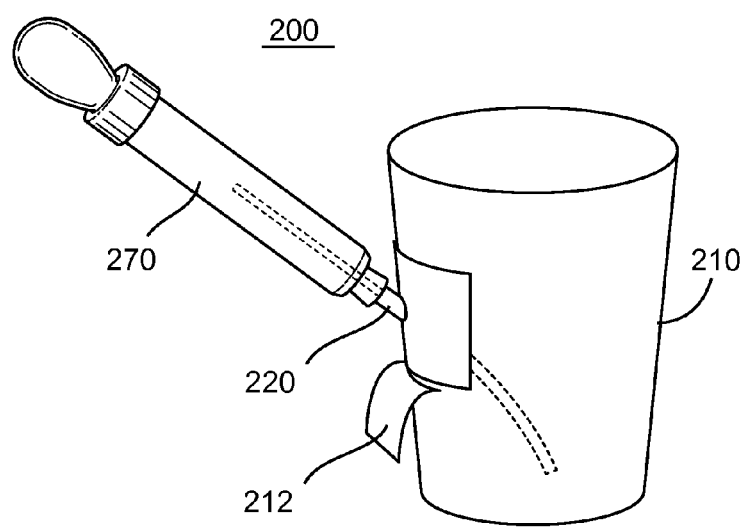

FIGS. 6A-6B show another embodiment of a collection container 200. FIG. 6A shows an unassembled view of collection container 200. FIG. 6B shows an assembled view of collection container 200.

Collection container 200 includes a receptacle 210, a handle attachment 220, and a handle 270.

Receptacle 210 is used for collecting urine, blood, saliva, or other liquid samples. Receptacle 210 has an open top, and may be cylindrical, rectangular, or any other suitable shape. Receptacle 210 may be made of a recyclable or biodegradable material. Receptacle 210 may be a commercially available paper or foam cup. Receptacle 210 may include a port 211. Port 211 may be formed in a side of receptacle 210. Alternatively, port 211 may be formed in a bottom or any other suitable location of receptacle 210. Receptacle 210 may include a removable seal 212 which keeps port 211 clean until ready for use.

Handle attachment 220 includes a handle extension 230, an attachment plate 250, and an aspiration tube 260.

Handle extension 230 includes a proximal end 232 and a distal end 234. Handle extension 230 includes a lumen 235. Handle extension 230 may be made of a substantially rigid material such as plastic or other suitable material. A fitting 233 is coupled to proximal end 232 of handle extension 230. Fitting 233 may be a luer-lock connector or any other suitable connector. Fitting 233 is capable of being coupled to a mating fitting on a mating device such as handle 270. Fitting 233 may be a female luer connector which is capable of being coupled to a male luer connector on a mating device. When coupled to receptacle 210, handle extension 230 and handle 270 may extend from receptacle 210 at an upward or ergonomic angle, which improves accessibility and allows the patient to maneuver and position receptacle 210, and maintain receptacle 210 in a substantially horizontal position during the collection of liquid samples Attachment plate 250 includes a proximal side 252 and a distal side 254. Proximal side 252 of attachment plate 250 is coupled to distal end 234 of handle extension 230. Attachment plate 250 includes an opening 255 in fluid communication with lumen 235 of handle extension 230. Attachment plate 250 may be made of a substantially rigid material such as plastic or other suitable material. Attachment plate 250 may be flat, curved, or otherwise configured to substantially follow the contour or shape of receptacle 210. Alternatively, attachment plate 250 may be made of a flexible material which allows attachment plate 250 to conform to the contour or shape of receptacle 210. Attachment plate 250 and handle extension 230 may be injection-molded as a single piece. Attachment plate 250 may include a double-sided tape 256. Alternatively, attachment plate 250 may be include an adhesive or any other suitable device which will not contaminate or react with a liquid sample in receptacle 210. When ready for use, attachment plate 250 is coupled to receptacle 210.

Aspiration tube 260 includes a proximal end 262 and a distal end 264. Proximal end 262 of aspiration tube 260 is coupled to distal side 254 of attachment plate 250. Aspiration tube 260 includes a lumen 265 in fluid communication with opening 255 of attachment plate 250. Aspiration tube 260 may be made of a flexible material such as polymer, plastic, or other suitable inert material. Aspiration tube 260 may be of sufficient length to reach the bottom or near the bottom of receptacle 210. Aspiration tube 260 may thus be able to reach most or all of a liquid sample in receptacle 210, even when the sample volume is very low. Aspiration tube 260 may include a sleeve 261 which covers and keeps aspiration tube 260 clean or sterile until handle attachment 220 is coupled to receptacle 210.

Attachment plate 250 may be coupled to a side of receptacle 210. Alternatively, attachment plate 250 may be coupled to a bottom or any other suitable location of receptacle 210. Receptacle 210 may have a pre-marked area which aids in the positioning of attachment plate 250. Attachment plate 250 may be coupled to an outside of receptacle 210, and aspiration tube 260 may pass through port 211. Alternatively, attachment plate 250 may be coupled to an inside of receptacle 210, and handle extension 230 may pass through port 211. Attachment plate 250 may serve to seal port 211 and prevent the liquid sample from escaping through port 211.

Handle 270 may serve as a transporting and dispensing device, such as the handles described in U.S. patent application Ser. No. 2006/0039833, which is incorporated by reference. A portion of a liquid sample in receptacle 210 may be transferred to handle 270 by creating a vacuum within handle 270 and drawing the liquid sample through lumen 265, opening 255, and lumen 235 and into handle 270. After a portion of the liquid sample has been transferred, handle 270 may be uncoupled from handle extension 230. Alternatively, handle 270 may be an elongate member made of a recyclable and/or biodegradable material such as cardboard or paper.

Figure 7A:
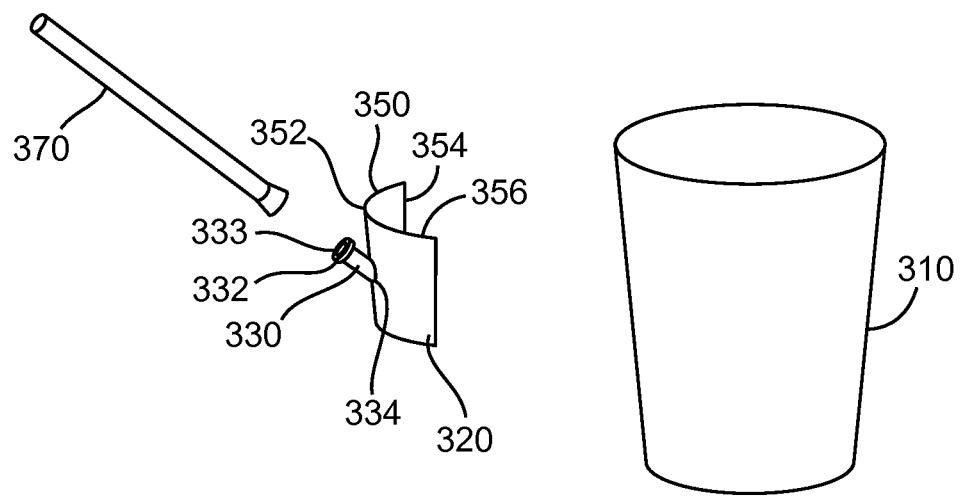
FIGS. 7A-7B show one embodiment of a handle attachment 320 for use with a receptacle 310.
Figure 7B:
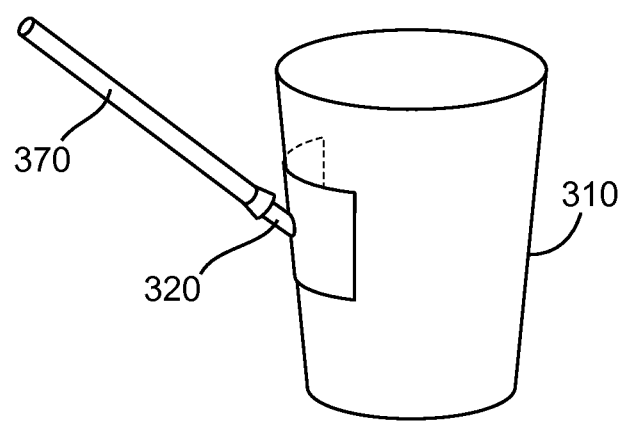

FIGS. 7A-7B show one embodiment of a handle attachment 320 and handle 370 for use with a receptacle 310. FIG. 7A shows an unassembled view of handle attachment 320, handle 370, and receptacle 310. FIG. 7B shows an assembled view of handle attachment 320, handle 370, and receptacle 310.

Collection container 300 includes a receptacle 310, a handle attachment 320, and a handle 370.

Receptacle 310 is used for collecting urine, blood, saliva, or other liquid samples. Receptacle 310 has an open top, and may be cylindrical, rectangular, or any other suitable shape. Receptacle 310 may be made of a recyclable or biodegradable material. Receptacle 310 may be a commercially available paper or foam cup.

Handle attachment 320 includes a handle extension 330 and an attachment plate 350.

Handle extension 330 includes a proximal end 332 and a distal end 334. Handle extension 330 may be made of a substantially rigid material such as plastic or other suitable material. A fitting 333 is coupled to proximal end 332 of handle extension 330. Fitting 333 may be a luer-lock connector or any other suitable connector. Fitting 333 is capable of being coupled to a mating fitting on a mating device such as a handle 370. Fitting 333 may be a female luer connector which is capable of being coupled to a male luer connector on a mating device. When coupled to receptacle 310, handle extension 330 and handle 370 may extend from receptacle 310 at an upward or ergonomic angle, which improves accessibility and allows the patient to maneuver and position receptacle 110, and maintain receptacle 110 in a substantially horizontal position during the collection of liquid samples Attachment plate 350 includes a proximal side 352 and a distal side 354. Proximal side 352 of attachment plate 350 is coupled to distal end 334 of handle extension 330. Attachment plate 350 may be made of a substantially rigid material such as plastic or other suitable material. Attachment plate 350 may be flat, curved, or otherwise configured to substantially follow the contour or shape of receptacle 310. Alternatively, attachment plate 350 may be made of a flexible material which allows attachment plate 350 to conform to the contour or shape of receptacle 310. Attachment plate 350 and handle extension 330 may be injection-molded as a single piece. Attachment plate 350 may include a double-sided tape 356 on distal side 354. Alternatively, attachment plate 350 may include an adhesive or any other device. When ready for use, attachment plate 350 is coupled to receptacle 310.

Attachment plate 350 may be coupled to a side of receptacle 310. Alternatively, attachment plate 350 may be coupled to a bottom or any other suitable location of receptacle 310. Receptacle 310 may have a pre-marked area which assists in the positioning of attachment plate 350.

Handle 370 may be an elongate member made of a recyclable and/or biodegradable material such as cardboard or paper.

Figure 7C:
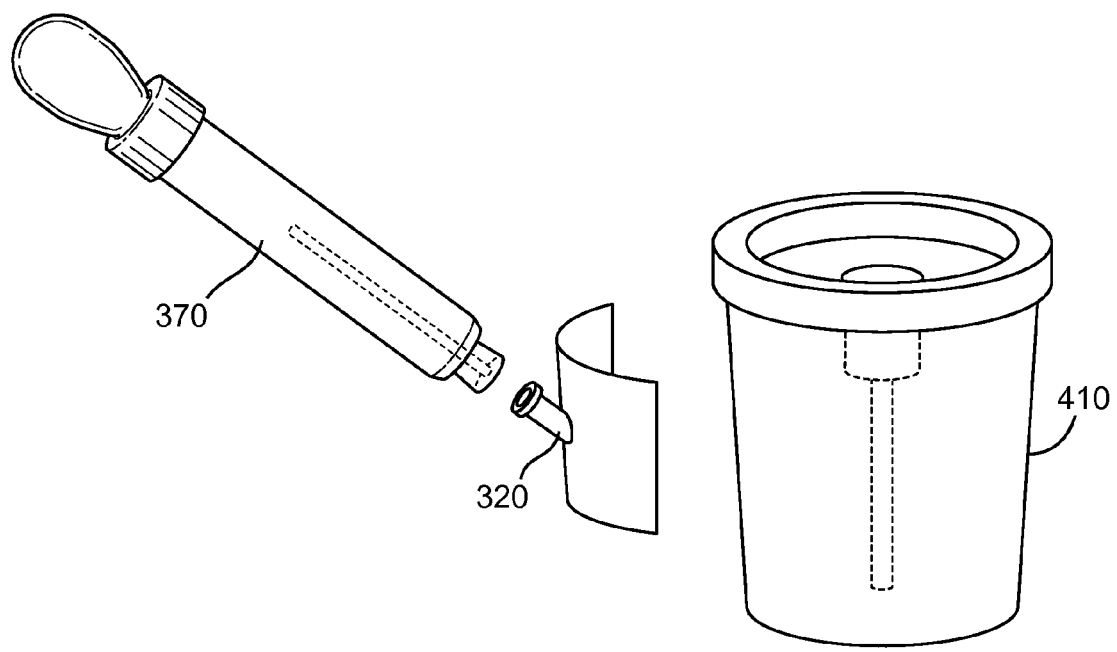
FIGS. 7C-7D show handle attachment 320 in use with a urine collection cup 410.
Figure 7D:
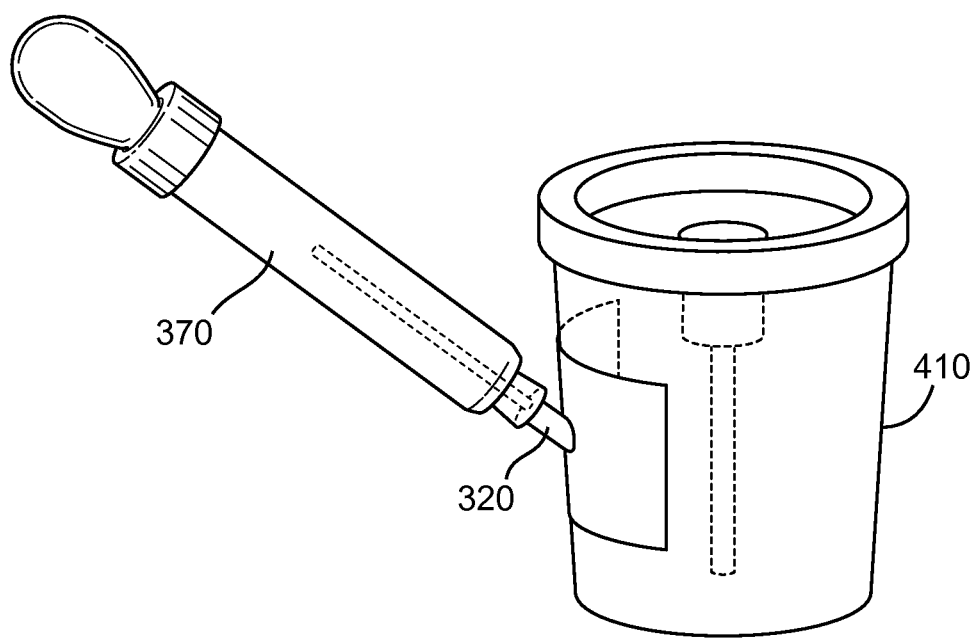

FIGS. 7C-7D show handle attachment 320 in use with a urine collection cup 410. FIG. 7C shows an exploded view of handle attachment 320 in use with a urine collection cup 410. FIG. 7D shows an assembled view of handle attachment 320 in use with a urine collection cup 410.

While the foregoing has been with reference to particular embodiments of the invention, it will be appreciated by those skilled in the art that changes in these embodiments may be made without departing from the principles and spirit of the invention.

All publications and patent applications mentioned in this specification are herein incorporated by reference to the same extent as if each individual publication or patent application was specifically and individually indicated to be incorporated by reference.

What is claimed is:

1. A collection container for a liquid sample, the collection container comprising:
   a receptacle including an open top;
   a handle extension including a proximal end and a distal end, the handle extension including a first lumen;
   a fitting coupled to the proximal end of the handle extension, the fitting capable of being coupled to a mating device;
   a middle section including a proximal end and a distal end, the proximal end of the middle section being coupled to the distal end of the handle extension, the middle section including a second lumen in fluid communication with the first lumen;
   an attachment plate coupled to the middle section and to the receptacle; and
   an aspiration tube including a proximal end and a distal end, the proximal end of the aspiration tube being coupled to the distal end of the middle section, the aspiration tube including a third lumen in fluid communication with the second lumen and with an interior of the receptacle, the distal end of the aspiration tube reaching substantially a bottom of the receptacle.

2. The collection container of claim 1, wherein the receptacle is collapsible.

3. The collection container of claim 1, wherein the fitting is a luer connector.

4. The collection container of claim 1, wherein the mating device is a handle including a mating fitting.

5. The collection container of claim 1, wherein the attachment plate is coupled to a side of the receptacle.

6. The collection container of claim 1, wherein the attachment plate is coupled to an inside of the receptacle.

7. The collection container of claim 6, further comprising:
   a port formed in a side of the receptacle, wherein the handle extension passes through the port.

8. The collection container of claim 1, wherein the attachment plate is coupled to an outside of the receptacle.

9. The collection container of claim 8, further comprising:
   a port formed in a side of the receptacle, wherein the aspiration tube passes through the port.

10. A collection container for a liquid sample, the collection container comprising:
    a receptacle including an open top;
    a port formed in a wall of the receptacle;
    an attachment plate coupled to the port, the attachment plate having a proximal side and a distal side, the attachment plate including an opening;
    a handle extension including a proximal end and a distal end, the distal end of the handle extension being coupled to the proximal side of the attachment plate, the handle extension having a first lumen in fluid communication with the opening of the attachment plate;
    an aspiration tube coupled to the distal side of the attachment plate, the aspiration tube including a second lumen in fluid communication with the opening of the attachment plate and an interior of the receptacle, the aspiration tube reaching substantially a bottom of the receptacle; and
    a fitting coupled to the proximal end of the handle extension, the fitting capable of being coupled to a mating device.

11. The collection container of claim 10, wherein the attachment plate is coupled to an outside of the receptacle, and the aspiration tube passes through the port.

12. The collection container of claim 10, wherein the attachment plate is coupled to an inside of the receptacle, and the handle extension passes through the port.

13. The collection container of claim 10, wherein the fitting is a luer connector.

14. The collection container of claim 10, wherein the mating device is a handle including a mating fitting.

15. A collection container for a liquid sample, the collection container comprising:
    a receptacle including an open top;
    an attachment plate having a distal side coupled to an outside of the receptacle;
    a handle extension having a distal end coupled to a proximal side of the attachment plate; and
    a fitting coupled to a proximal end of the handle extension, the fitting capable of being coupled to a mating device.

16. The collection container of claim 15, wherein the handle extension extends from the receptacle at an upward angle.

17. The collection container of claim 15, wherein the fitting is a luer connector.

18. The collection container of claim 15, wherein the mating device is a handle including a mating fitting.

* * * * *